(12) United States Patent
Galehr

(10) Patent No.: US 8,402,624 B2
(45) Date of Patent: *Mar. 26, 2013

(54) BLANK ARRANGEMENT

(75) Inventor: Klaus Galehr, Schlins (AT)

(73) Assignee: Ivoclar Vivadent AG, Schaan (LI)

( * ) Notice: Subject to any disclaimer, the term of this patent is extended or adjusted under 35 U.S.C. 154(b) by 754 days.

This patent is subject to a terminal disclaimer.

(21) Appl. No.: 12/231,121

(22) Filed: Aug. 29, 2008

(65) Prior Publication Data

US 2009/0075238 A1   Mar. 19, 2009

(30) Foreign Application Priority Data

Sep. 14, 2007 (DE) .......................... 10 2007 043 837

(51) Int. Cl.
*B25B 27/41* (2006.01)
*A61C 11/00* (2006.01)

(52) U.S. Cl. ...................................... 29/281.1; 433/213

(58) Field of Classification Search .............. 29/281.1, 29/557, 896.1; 428/542.8; 433/49, 213; 409/219, 234; 269/287

See application file for complete search history.

(56) References Cited

U.S. PATENT DOCUMENTS

| | | | |
|---|---|---|---|
| 4,615,678 | A | 10/1986 | Moermann et al. |
| 5,342,696 | A | 8/1994 | Eidenbenz et al. |
| 6,224,371 | B1 | 5/2001 | de Luca |
| 6,485,305 | B1 | 11/2002 | Pfeiffer |
| 6,627,327 | B2 | 9/2003 | Reidt et al. |
| 6,640,150 | B1 * | 10/2003 | Persson et al. ................ 433/213 |
| 6,660,400 | B1 * | 12/2003 | Hintersehr ................ 428/542.8 |
| 6,905,293 | B1 | 6/2005 | Filser et al. |
| 6,991,853 | B2 | 1/2006 | de Luca et al. |
| 7,077,391 | B2 | 7/2006 | Filser et al. |
| 7,214,435 | B2 | 5/2007 | Meyertholen et al. |
| 7,255,562 | B2 | 8/2007 | Rusin et al. |
| 2004/0120781 | A1 * | 6/2004 | Luca et al. ...................... 29/557 |
| 2005/0008989 | A1 | 1/2005 | Rothenberger et al. |
| 2005/0276672 | A1 * | 12/2005 | Prince et al. .................. 409/234 |
| 2007/0172787 | A1 | 7/2007 | Fornoff |

FOREIGN PATENT DOCUMENTS

| | | |
|---|---|---|
| AU | 8090901 | 2/2002 |
| DE | 19714223 | 10/1998 |
| DE | 197 33 161 A1 | 2/1999 |
| DE | 10 2004 020 192 A1 | 10/2005 |
| DE | 102004020192 | 10/2005 |
| EP | 2384718 | 9/2011 |
| JP | 7-28878 | 4/1995 |
| WO | WO 020961 A1 * | 2/2002 |

OTHER PUBLICATIONS

European Search Report, Sep. 21, 2011 (EP' 516).

* cited by examiner

*Primary Examiner* — Hadi Shakeri

(74) *Attorney, Agent, or Firm* — Ann M. Knab; Thad McMurray

(57) ABSTRACT

The invention relates to a blank arrangement, with a blank (12) that is to be machined, in particular for the production of dental restoration parts. The blank is connected to a holder (16), which is fixedly connected to the blank (12), and to an adapter (22), which releasably bears the holder (16) and the blank (12), the adapter (22) having an effective surface by means of which the blank unit can be mounted in or on the work holding fixture of a machining device.

11 Claims, 4 Drawing Sheets

BLANK ARRANGEMENT

CROSS-REFERENCE TO RELATED APPLICATIONS

This application claims foreign priority benefits under 35 U.S.C. §119 from German patent application Ser. No. 10 2007 043 837.2 filed Sep. 14, 2007.

TECHNICAL FIELD

The invention relates to a blank arrangement, in particular for the production of dental restoration parts, with a blank that is to be machined, in particular made of dental material and suitable for the production of dental restoration parts, the blank being adhesively secured to a holder which has a portion received within an adapter.

BACKGROUND OF THE INVENTION

Blanks for dental restoration parts are typically machined, in order to achieve an adaptation to the desired shaping. While precision work and adjustments have to be performed in the adaptation of the dental restoration part by the dentist, or generally by the dental technician, typically blanks produced in block form are brought into shape in advance, in order to restrict the adaptation work to a reasonable amount.

This applies to a particular extent to dental restoration parts and corresponding blanks made of ceramic. Ceramic materials—especially zirconium dioxide—are particularly hard, so that it is desirable to reduce the machining that has to be performed in the dental laboratory to a minimum.

On the other hand, ceramic blanks can be produced exceedingly well in block form. Therefore, based on the suitably selected raw material, a blank is pressed in block form and sintered in a sintering furnace.

With regard to the particular hardness of ceramics, such as for example zirconium-based ceramics, it has also already become known not to machine the fully sintered product, which is very hard, but a pre-sintered product, which already has sufficient stability for machining. As a result, the wear of the tools that are used for the machining, that is to say for example milling cutters or turning tools, can also be distinctly reduced.

For the machining, the blank must be received in a suitable way in the work holding fixture of the machining device. Often used for this purpose is a holding pin, the outer shape of which is formed suitably for the work holding fixture and is cemented in a bore in the blank. See for example U.S. Pat. Nos. 6,224,371 and 6,627,327. However, to this extent the anchoring of the blanks for the machining is extremely complicated and also susceptible to errors. In particular, it must be ensured that a predetermined position is ensured for the fixing between the pin, which is held in the work holding fixture, and the blank.

Furthermore, it has also already been proposed to configure a support with an adhesive area, on which the blank is adhesively attached. See for example U.S. Pat. Nos. 4,615,678, 7,214,435, and 7,255,562. This also allows in particular blanks of different sizes to be used with the same work holding fixture fixing pin. Typically, such an adhesive area is planar, in order to ensure a particularly good contact with a surface of the blank, which is initially in block form. As a result of this, the spatially fixed fixing of the blank is difficult, and it is typical in the case of such a configuration to resort to forming a differential dimension, which relates a side face of the blank to a side face of the insert pin, and using this as a basis for fixing the connection between the insert pin and the blank. This is indeed possible in principle and can also be automated by machine, which is necessary with regard to the numbers of items to be produced.

However, precisely in the case of different work holding fixtures, it is necessary to use different insert pins, which accordingly have different dimensions. However, the combination of such different insert pins, in a number corresponding to the work holding fixtures used, with different blanks leads to a multiplication of the possible combinations, so that fixing such a differential value would be significantly too complicated in practice and therefore this has not been widely adopted for understandable reasons.

It has also been proposed to provide a blank which is attached to a support plate mounted on a holder section that is received by a boring inside a shaft part of a holding device. See German Patent 197 33 161. In this design a clamping screw is used to fix the holder section into position. A groove extending around the outside of the holder section mantle receives at least part of the screw, which is smaller than or equal in size to the groove.

OBJECTS AND SUMMARY OF THE INVENTION

Therefore, the invention is based on the object of providing a blank arrangement with a blank that is to be machined, in particular made of dental material and suitable for the production of dental restoration parts, that is also reliably suitable for the industrial-scale production of adapted, that is to say machined, blanks.

According to the invention, it is particularly favorable that, by providing a separate holder, a unique assignment between the relative position of the blank and a reference point of the holder that is to be arbitrarily chosen is possible. This is in principle independent of a configuration of an effective surface of the adapter provided according to the invention, which ensures engagement with respect to the work holding fixture. The effective surface can consequently be kept in any desired suitable form, and even be complicated, so that it is possible to make it compact, without having to pay any regard to the dimensioning and relative arrangement of the blank.

Blanks of various sizes can accordingly be readily attached centrally on an end face of the holder and adjusted with respect to the shank of the latter. Once the relative position of the shank, which is guided in a corresponding recess in the adapter, is known for each configuration of the adapter, and consequently the corresponding work holding fixture, the number of dimensionings required according to the invention is still practicable. If, for example, 20 different work holding fixtures are to be combined with 30 different blanks, the provision of the sum of the corresponding dimensions, that is to say 50 dimensions, is required according to the invention, while theoretically, in the case of solutions without the invention that have a corresponding number of work holding fixtures and blanks, 20×30, that is to say 600, sizes would have to be kept in stock, which is out of the question in practice. It is surprisingly found according to the invention that the division into a holder and an adapter reduces the organizational effort involved.

According to the invention, the holder may be fastened to the blank in any desired suitable way. For example, the blank may laterally protrude distinctly beyond the holder and be placed on an end face of a plate which closes off the holder at the top.

It is particularly favorable according to the invention that the holder, which carries the blank, and can be handled separately from the adapter, allows a connection that can always be established with the same automatic adhesive dispenser to be established between the holder and the blank. To this extent, the automatic adhesive dispenser therefore does not have to be converted, or a new dispenser obtained, when blanks for other work holding fixtures are to be handled. This represents a considerable advantage specifically in the case of the industrial production of dental restoration parts in large numbers, specifically also in the case of the use of ceramic blocks as blanks.

The blank arrangement according to the invention has with preference an adapter which is provided with always the same receptacle for the holder. This ensures that blanks can be securely held in the work holding fixture independently of the shaping of the work holding fixture. Surprisingly, the security is not impaired by the additional connection having to be established between the holder and the adapter.

The accuracy of the fit with which the adapter receives the holder is chosen with preference such that, when the connection is established, the holder and the adapter act virtually as one piece, even if a separation is in fact possible.

If need be, the securement can be further improved by a partially resilient configuration of the transition between the holder and the adapter, it being self-evident that a comparatively hard spring is used with preference, one which can withstand the machining forces of the tool of the machining device.

It is particularly favorable according to the invention whenever the holder is designed such that it can transfer shearing forces particularly well, both with respect to the adapter and with respect to the blank. For this purpose, it is possible for example to allow a short and comparatively sturdy connector to enter a blind-hole bore of the adapter, to be precise with exact-fitting guidance. The force transfer with respect to the blank can be further assisted by the adapter having lateral supporting flanges in the form of a collar, which provides solid support for a plate or a corresponding flange of the holder there. Compressive forces, that is to say forces in the axial direction, can also be absorbed well in this way.

In the case of this embodiment, the receptacles between the holder and the adapter have virtually the form of "T"s, which are inserted one in the other.

It is self-evident that any other desired configuration of the holder and the adapter and their transition is possible. By providing a comparatively thin supporting surface of the holder, which is supported by a corresponding supporting collar or an end face of the adapter, a wide end face of the holder can also be provided as an adhesive area with comparatively little expenditure in terms of material.

The blank, the holder and the adapter may be shaped here in any suitable way desired. Both round configurations and configurations deviating from a circular shape are possible in each case, but it is in any event preferred that the connection between the adapter and the holder is fixed in terms of rotation and secure in terms of moments, that is to say withstands both shearing forces and rotational forces that may be introduced into the blanks by the machining device during the machining.

It is particularly favorable according to the invention if an end face of the holder provides an area that is flat and to which adhesive adheres well, the extent of which corresponds at least to the extent of the ceramic block (considered in the respective direction). This ensures that a supporting surface that is as large as possible is available for the adhesive connection, since lateral machining forces on the blank must be absorbed by the adhesive connection, so that a wide contact area between the holder and the blank reduces the forces of detachment.

It is particularly favorable according to the invention if the pluggability of the holder into or onto the adapter is provided by simple means and the release of the connection is also quickly possible as and when required. Any desired suitable connecting techniques are suitable for this purpose, it being self-evident that it is particularly favorable if rotational forces can also be transferred in a way that is secure in terms of moments.

It is particularly favorable according to the invention that the holder for the blank has an end face that faces away from the adapter and on which the blank can be received.

It is particularly favorable according to the invention that the holder has a round or angular plate, the face of which that faces away from the adapter carries the blank.

It is particularly favorable according to the invention that the blank is fastened to the holder with surface area contact and protrudes beyond the holder at at least one point.

It is particularly favorable according to the invention that the blank is fastened to the holder with an interference fit.

It is particularly favorable according to the invention that the blank is adhesively attached, welded and/or bonded on the holder.

It is particularly favorable according to the invention that the blank and the holder are at least partially pressed one into the other or screwed one onto the other or in some other way connected to each other with a form fit.

It is particularly favorable according to the invention that the holder and the blank are braced against each other and that the pre-stressing of the bracing is in particular greater than the machining force produced by the machining device.

It is particularly favorable according to the invention that the holder has a connecting region for the blank, which in particular offers flange-like projections and is formed with particular preference in the form of a plate and from which there extends a shank, which interacts with the adapter.

It is particularly favorable according to the invention that the holder has a shank which is formed for being received in the adapter, in particular for being received in the adapter with a form fit. It is particularly favorable according to the invention are the holder is fixed with respect to the adapter in a rotationally locked manner and in particular has a stop facing in the axial direction.

It is particularly favorable according to the invention that the shank is received in a blind hole of the adapter, in particular in the upper region thereof.

It is particularly favorable according to the invention that the shank of the holder ends above an undercut, which forms an effective surface with respect to the work holding fixture of the machining device and, in particular, offers a form fit there.

It is particularly favorable according to the invention that the shank of the holder has at least one undercut, which in particular runs at least partially around it.

It is particularly favorable according to the invention that the holder, in particular its shank, has a bore or an internal thread for the fixing in the adapter, which in particular matches a through-bore in the adapter.

It is particularly favorable according to the invention that the holder, in particular its shank, the adapter and/or the blank have a marking, in particular a mechanical or colored marking, which symbolizes the fitting together of corresponding parts of the blank arrangement.

It is particularly favorable according to the invention that the holder, in particular it shank, the adapter and/or the blank have a barcode, in particular a mechanical or colored barcode, which symbolizes the fitting together of corresponding parts of the blank arrangement.

It is particularly favorable according to the invention that the holder, in particular its shank, the adapter and/or the blank have a sensor, a transmitter and/or a chip, by means of which the use of the respectively relevant type of blank, holder and/or adapter can be signalled.

It is particularly favorable according to the invention that the holder and/or the adapter have a predetermined breaking point, which yields under loading in the machining device.

It is particularly favorable according to the invention that at least two adapters are provided and have different effective surfaces that can be inserted into the work holding fixtures of different machining devices, and wherein the at least two adapters have receptacles that are the same as each other for the holder.

It is particularly favorable according to the invention that the connection between the holder and the adapter is secured such that it is free from vibrations.

According to a further advantageous configuration, it is provided that the blank is fastened to the holder with surface area contact and that the holder protrudes beyond the blank at at least one point.

According to a further advantageous configuration, it is provided that the blank and the holder are at least partially pressed one into the other or screwed one against the other, or in some other way connected to each other.

According to a further preferred configuration, it is provided that the blank and the holder are fixedly connected to each other or fixedly braced one against the other such that the pre-stressing of the bracing or the holding force of the connection is greater than the machining force produced by the machining device.

According to a further advantageous configuration, it is provided that the blank arrangement according to the invention forms on the holder a flange, which is formed in particular in the form of a plate and from which there extends a shank or an insert stub, which interacts with the adapter.

According to a further advantageous configuration, it is provided that a shank of the holder is suitably formed for being received in the adapter, in particular for being received in the adapter with a form fit.

According to a further advantageous configuration, it is provided that the shank is formed as an insert stub and is received in a receptacle or a blind hole of the adapter, in particular in the upper region thereof.

According to a further advantageous configuration, it is provided that the shank of the holder ends above an undercut, which forms the effective surface with respect to the work holding fixture of the machining device and, in particular, offers a form fit there.

According to a further advantageous configuration, it is provided that the holder and/or the blank and/or the adapter have a marking or a coding, which symbolizes the fitting together of corresponding parts of the blank arrangement. The marking may also be formed as a mechanical or colored barcode.

BRIEF DESCRIPTION OF THE FIGURES

Further advantages, details and features emerge from the following description of two exemplary embodiments of the invention on the basis of the drawing, in which.

DETAILED DESCRIPTION

Figure 1:
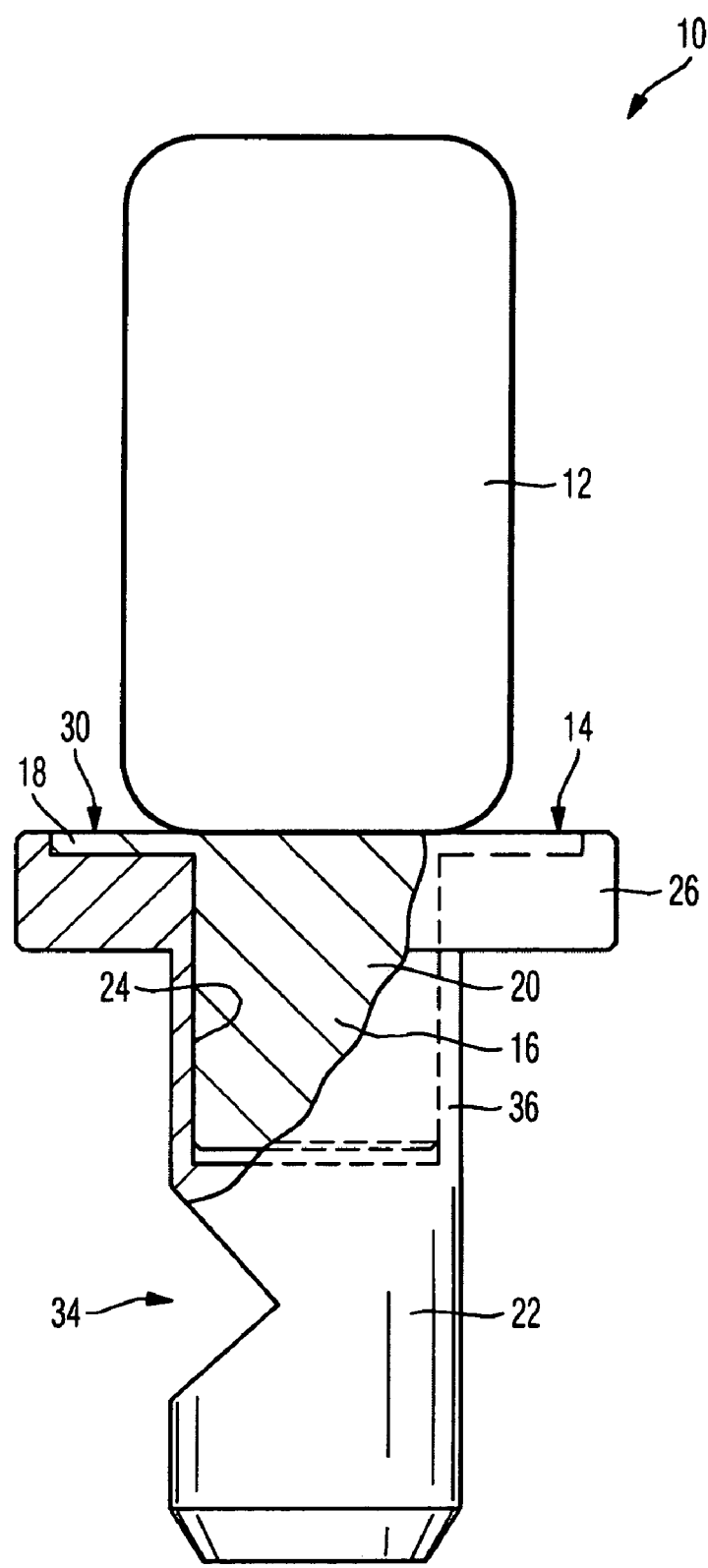
FIG. 1 shows a schematic side view of an embodiment of a blank arrangement according to the invention.

The blank arrangement 10 represented in FIG. 1 has a blank 12, which is adhesively attached on an end face 14 of a holder 16. With preference, the blank 12 is a cuboidal ceramic element with rounded corners. It is intended for being machined, in order to produce a dental restoration part. For this purpose, it lies with one of its side faces flush against the end face 14. The type of adhesive bonding that is used according to the invention is known in the prior art, it being self-evident that the holding forces of the adhesive connection distinctly exceed the forces that are introduced onto the blank during the machining.

The holder 16 is formed in a substantially T-shaped manner. It has a peripheral flange 18, the extent of which distinctly exceeds the width of the blank 12, so that blanks of distinctly greater dimensions can also be received there.

Furthermore, the holder 16 has an insert stub 20, which is substantially of the same height and width, or else—as in the exemplary embodiment represented—a length or height that exceeds the width by no more than 50%. In the exemplary embodiment represented, the height/width ratio is 1.4:1.

In the exemplary embodiment represented, the holder 16 is received in a completely recessed manner in the adapter 22. For this purpose, the adapter 22 has a receptacle 24, which is formed in the manner of a blind-hole bore and in its dimensions exactly matches the insert stub 20. Accordingly, in the exemplary embodiment represented the receptacle 24 is formed as a blind hole.

Supporting the flange 18 of the holder 16, the adapter 22 also has a lateral supporting flange 26, which is formed in the manner of a collar and likewise give the adapter 22, when viewed in cross section, substantially the shape of a T. The supporting flange 26 of the adapter have a distinctly greater material thickness than the flange 18 of the holder, a ratio of 4:1 being provided for example, but a ratio between 2:1 and 10:1 also being possible.

In the exemplary embodiment represented, the flange 18 is also received in a recessed manner in a depression 30 of the supporting flange 26. It is self-evident that this measure is optional. If such an arrangement is provided, it is also possible to form a means for preventing twisting between the holder 16 and the adapter 22 on the outer circumference of the flange 18 or on the outer circumference of the depression 30.

Alternatively, a means for preventing twisting may also be provided by corresponding shaping of the insert stub 20 and the receptacle 24, which is formed as a blind hole, in that these two parts are given a shape deviating from the shape of a circle, at least at one point.

In the exemplary embodiment represented, the adapter 22 is shaped in a particular way, in order to allow it to be received in a special work holding fixture of a machining device, which is not represented here. For this purpose, in the case of the example a right-angled notch 34 is formed as an undercut. The notch 34 extends under the blind hole 24, so that it does not impair the reception of the holder 16 there. Corresponding work holding fixtures are known and may be designed in any desired suitable way, with numerous different work holding fixtures being in existence, specifically dependent on the milling machine manufacturer.

If the blank 12 is to be machined in a machining device other than the one represented here, the adapter 22 can be readily exchanged, and replaced by another adapter 22, which however has exactly the same receptacle 24, so that the same holder 16 can be inserted.

The connection between the adapter 22 and the holder 16 is free from play, so that the removal of the holder 16 from the adapter 22 is possible merely with a certain force. In the exemplary embodiment represented, the lateral material thickness of the adapter 22 around the insert stub 20 is quite small. The side wall 36 provided there may, if need be, also be prestressed inward, so that it curves inwardly somewhat when the holder 16 is not inserted. Receiving the holder 16 then has the effect that the side wall 36 lies under prestress against the side faces of the insert stub 20.

Since the same holder can always be used, the adapter can be adhesively attached extremely easily in an exact position on the holder. This can take place for example by the same degree of prestress of the flange 18 with respect to the insert stub 20 always being used, and the blank 12, the width of which is fixed and varies from blank to blank, being adhesively attached at a predetermined distance from the edge of the flange 18. It is also possible for such an adhesive connection to be provided by means of an automatic adhesive dispenser.

Figure 2:
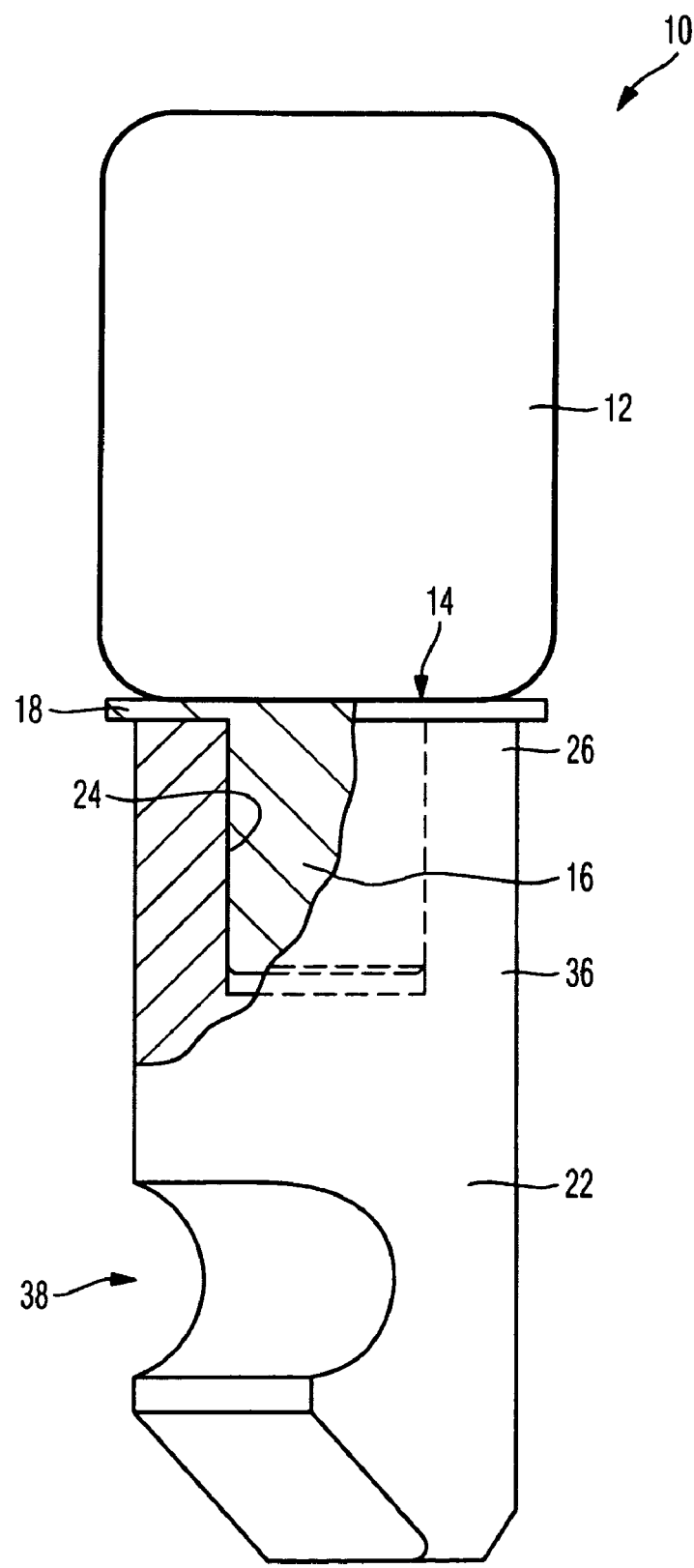
FIG. 2 shows a view of a further embodiment of a blank arrangement according to the invention.

A modified configuration of an adapter can be seen in FIG. 2. There, the same designations indicate the same or corresponding parts. In the case of this configuration, the adapter 22 has a greater diameter and is intended for a different work holding fixture, in the case of which a specially shaped undercut 38 is provided instead of the notch 34. On the other hand, the receptacle 24 is shaped in the same way as in the case of the embodiment according to FIG. 1 of the adapter, and the holder 16 corresponds to the holder represented in FIG. 1. The holder 16, in particular its shank 20, has a bore or an internal thread for the fixing in the adapter 22, which in particular matches a through-bore in the adapter.

In the exemplary implement represented, a somewhat wider blank 10 is provided, which accordingly rests with a greater width on the end face 14 of the holder 16. Although the flange 18 is laterally supported, in the case of this embodiment of the adapter 22 the supporting flange 26 is not formed in the manner of a collar, but is formed directly by the side walls 36 of the adapter 22.

It should be appreciated that blanks of various sizes can accordingly be readily attached centrally on an end face of the holder and adjusted with respect to the shank of the latter. Once the relative position of the shank, which is guided in a corresponding recess in the adapter, is known for each configuration of the adapter, and consequently the corresponding work holding fixture, the number of dimensionings required according to the invention is still practicable. If, for example, 20 different work holding fixtures are to be combined with 30 different blanks, the provision of the sum of the corresponding dimensions, that is to say 50 dimensions, is required according to the invention, while theoretically, in the case of solutions without the invention that have a corresponding number of work holding fixtures and blanks, 20×30, that is to say 600, sizes would have to be kept in stock, which is out of the question in practice. It is surprisingly found according to the invention that the division into a holder and an adapter reduces the organizational effort involved. The above is facilitated by providing the holder 16 and the adapter 22 with suitable indicia, for example mechanical markings, color markings, and barcodes. In addition this can also be facilitated by providing the blank 12, the holder 16, and/or the adapter 22 with a sensor, chip and/or transmitter by means of which the respective relevant type of blank, holder and/or adapter can be signalled.

Figure 3:
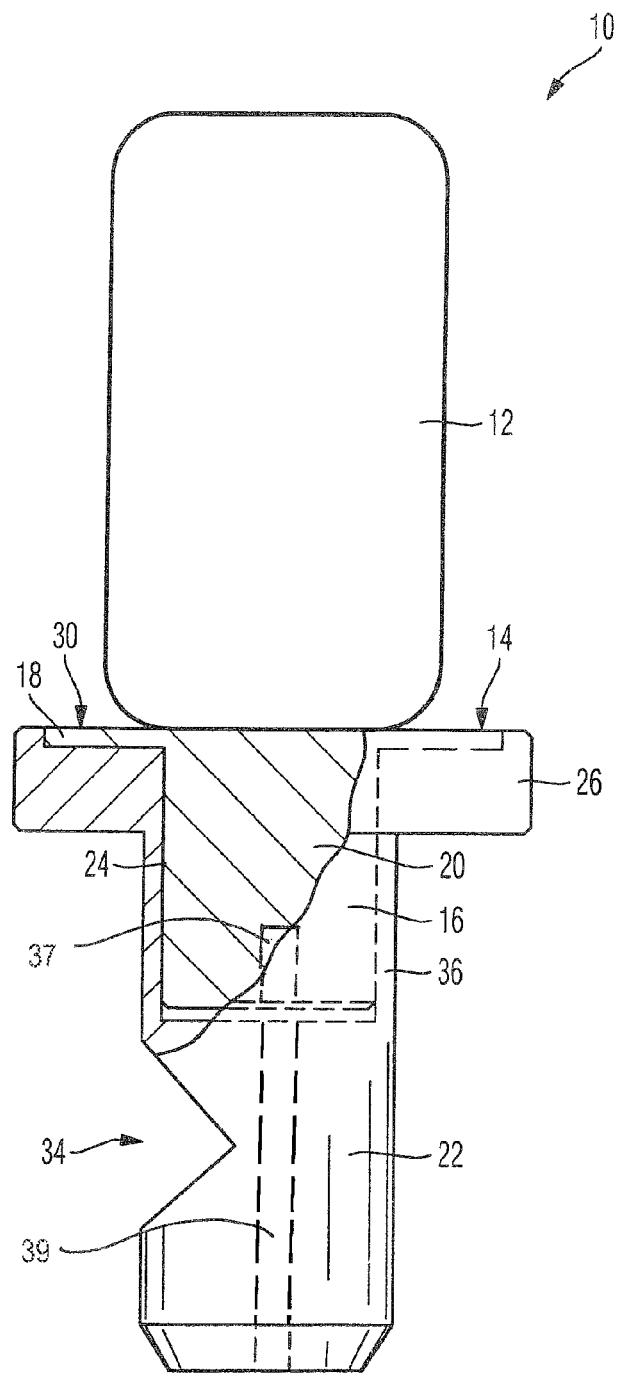
FIG. 3 shows a view of a further embodiment of a blank arrangement according to the invention.
Figure 4:
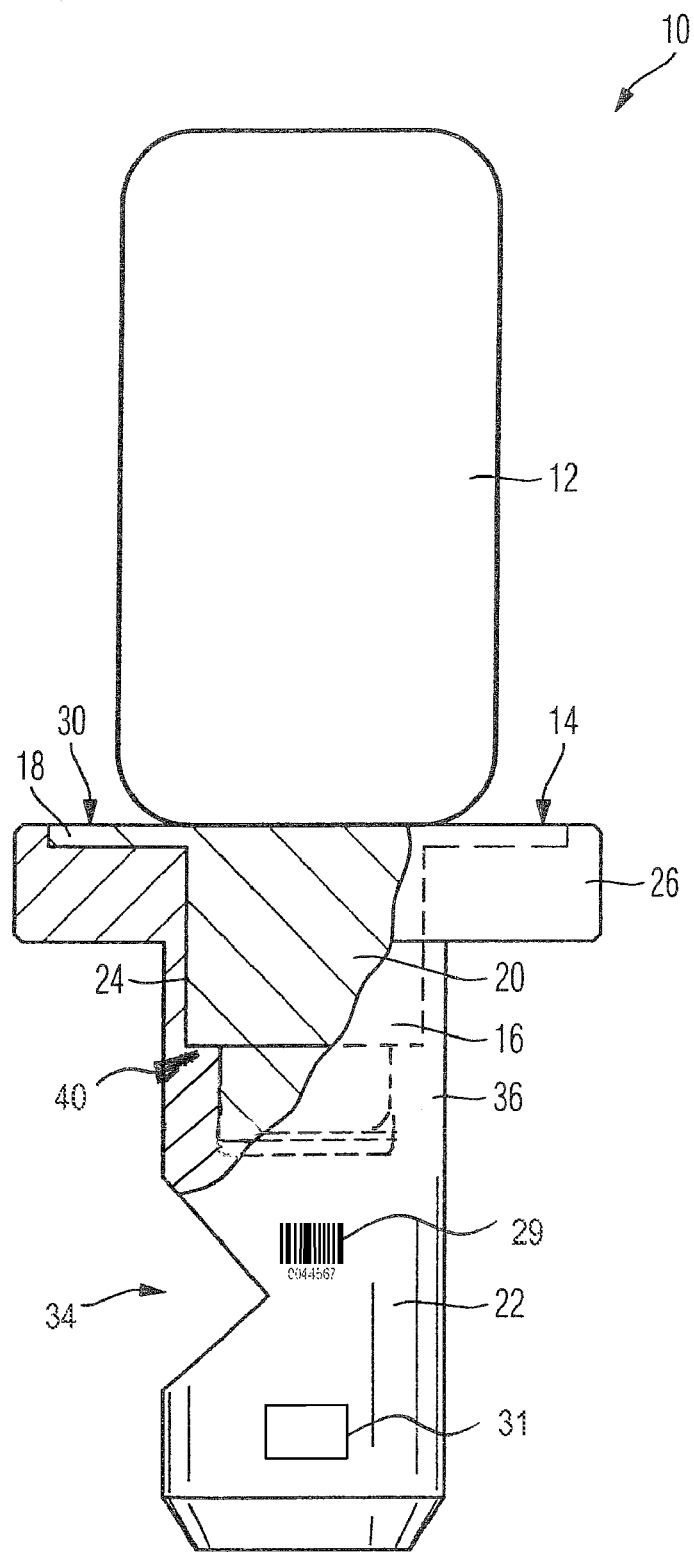
FIG. 4 shows a view of a further embodiment of a blank arrangement according to the invention.

FIG. 3 shows an option for connection of the holder (16) to adapter (22). Shank (20) of holder (16) includes a bore or internal thread (37) which matches a through-bore (39) in adapter (22). FIG. 4 shows additional elements of the invention. Marking or bar code (29) is displayed on adapter (22) for identifying corresponding parts of the blank arrangement. Similar marking or bar code may be also used on the blank (12) and holder (16) for identifying corresponding parts of the blank arrangement. A transmitter, chip or sensor (31) on adapter (22) can signal the relevant type of adapter. A similar transmitter, chip or sensor may be used on the blank (12) and the holder (16) to signal the relevant type of blank or holder. For both FIGS. 3 and 4, the same designations indicate the same or corresponding parts as in FIGS. 1 and 2.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A blank arrangement, with a blank (12) that is to be machined, the blank made of dental material and suitable for the production of dental restoration parts; the blank arrangement comprising:
    a blank (12);
    a holder (16) which is fixedly connected to the blank (12); and
    an exchangeable adapter (22) connected to the holder (16), the adapter (22) having an effective surface, by means of which the blank arrangement can be releasably fastened in or on a work holding fixture of a machining device;
    wherein the holder (16) comprises a shank for form-locking reception within the adapter;
    wherein the holder (16) has an end face (14) on which the blank can be received, the end face being formed on a flange portion (18) of the holder, and wherein the adapter (22) has a flange portion (26) having at least one depression for receipt of the flange portion (18) of the holder.

2. The blank arrangement as claimed in claim 1, wherein the holder (16) is provided with a shank which has a bore or an internal thread for the fixing in the adapter (22), which matches a through-bore in the adapter (22).

3. The blank arrangement as claimed in claim 1, wherein the blank (12), the holder (16) and/or the adapter (22) have a marking and/or coding.

4. The blank arrangement as claimed in claim 3, wherein the marking and/or coding, comprise a mechanical or colored marking for identifying corresponding parts of the blank arrangement.

5. The blank arrangement as claimed in claim 1, wherein the shank, the holder (16) and/or the adapter (22) have a barcode for identifying corresponding parts of the blank arrangement.

6. The blank arrangement as claimed in claim 5, wherein the barcode comprises a mechanical or colored barcode for identifying corresponding parts of the blank arrangement.

7. The blank arrangement as claimed in claim 1, wherein the blank (12), the holder (16) and/or the adapter (22) have a sensor, a transmitter and/or a chip by means of which the use of the respective relevant type of blank, holder, and/or adapter can be signalled.

8. The blank arrangement as claimed in claim 1, wherein the holder (16) and/or the adapter (22) have a predetermined breaking point, which yields under loading in the machining device.

9. The blank arrangement as claimed in claim 1, wherein at least two adapters (22) are provided and have different effective surfaces that can be inserted into the work holding fixtures of different machining devices, and wherein the at least two adapters (22) have receptacles (24) that are the same as each other for the holder (16).

10. The blank arrangement as claimed in claim 1, wherein the shank (20) is formed in a stepped manner and has at least two cross-sectional regions with different diameters.

11. The blank arrangement as claimed in claim 1, wherein the adapter comprises a receptacle (24) formed in a stepped manner and has at least two cross-sectional regions with different diameters.

* * * * *